United States Patent [19]
Shirai et al.

[11] Patent Number: 6,073,340
[45] Date of Patent: Jun. 13, 2000

[54] METHOD OF PRODUCING LAMINATION TYPE CERAMIC HEATER

[75] Inventors: Makoto Shirai, Kuwana; Akira Fujii, Yokkaichi; Masayuki Kobayashi, Kuwana, all of Japan

[73] Assignee: Denso Corporation, Japan

[21] Appl. No.: 09/087,149

[22] Filed: May 29, 1998

[30] Foreign Application Priority Data

May 29, 1997 [JP] Japan ................................ 9-158068
Jun. 30, 1997 [JP] Japan ................................ 9-190692

[51] Int. Cl.$^7$ ........................................ H05B 3/00
[52] U.S. Cl. ........................ 29/611; 29/619; 219/552; 219/542; 338/254
[58] Field of Search .................... 29/602.1, 611, 29/851, 591; 174/52, 68.5; 219/552, 542; 338/240, 238, 239, 241, 242, 274

[56] References Cited

U.S. PATENT DOCUMENTS

| | | | |
|---|---|---|---|
| 3,812,442 | 5/1974 | Muckelroy | 29/602 |
| 4,164,539 | 8/1979 | Johnston | 422/96 |
| 4,636,293 | 1/1987 | Bahya et al. . | |
| 5,379,004 | 1/1995 | Marusawa et al. | 333/1.1 |
| 5,451,748 | 9/1995 | Matsuzaki et al. . | |
| 5,486,682 | 1/1996 | Rysemus | 219/544 |

FOREIGN PATENT DOCUMENTS

| | | | |
|---|---|---|---|
| 2-26223 | of 0000 | Japan . | |
| 0044887 | 4/1978 | Japan | 29/611 |
| 1-123759 | 5/1989 | Japan . | |
| WO 94/14057 | of 0000 | WIPO . | |

Primary Examiner—Lee Young
Assistant Examiner—Sean Smith
Attorney, Agent, or Firm—Nixon & Vanderhye PC

[57] ABSTRACT

Several heater patterns are printed on a ceramic green sheet for substrates, and the ceramic green sheet is laminated with a ceramic green sheet for cover plates, thereby forming a lamination body. Then, the lamination body is cut so that it is divided into several intermediate bodies, each of which holds a corresponding one of the heater patterns therein and has a side surface on which a terminal portion of the heater pattern is exposed. Then, the intermediate body is baked. As a result, a ceramic heater composed of a heater substrate holding the heater pattern and a cover plate disposed on the heater substrate to cover the heater pattern can be provided without any micro-cracks therein.

23 Claims, 12 Drawing Sheets

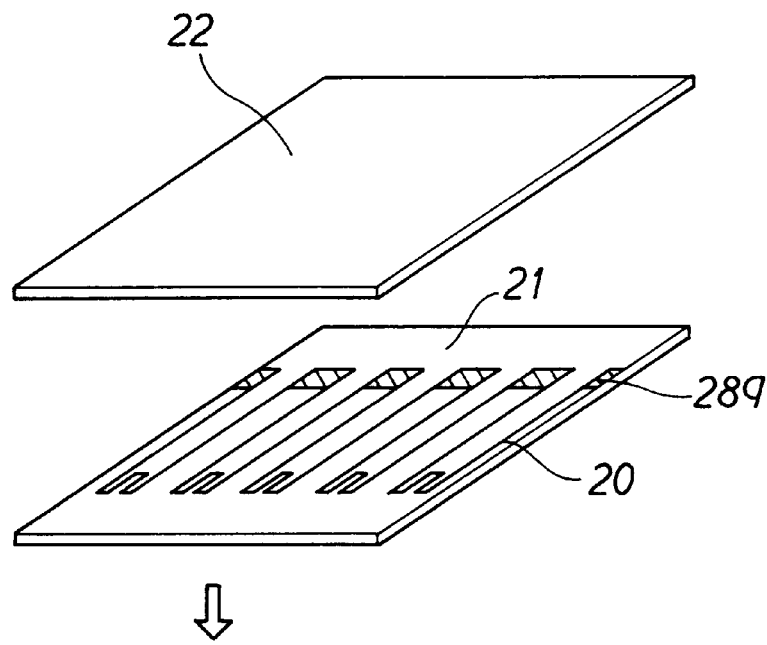
FIG. 4A
FIG. 4B
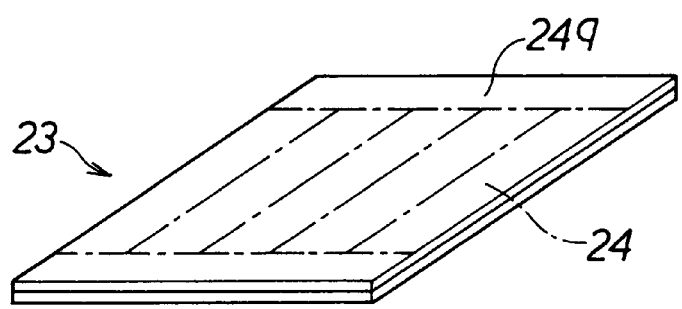
FIG. 4C
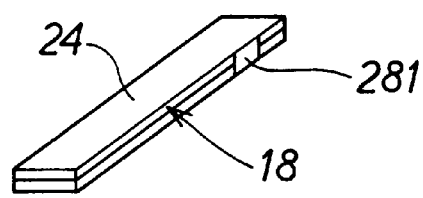
FIG. 4D
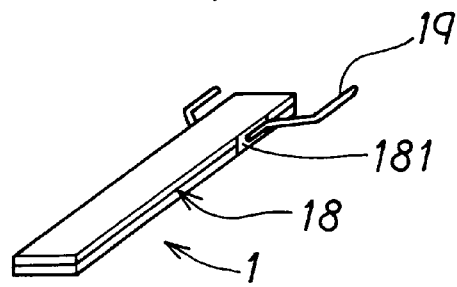

6,073,340

METHOD OF PRODUCING LAMINATION TYPE CERAMIC HEATER

CROSS REFERENCE TO RELATED APPLICATIONS

This application is based upon and claims the benefit of priority of the prior Japanese Patent Applications No. 9-158068 filed on May 29, 1997, and No. 9-190692 filed on Jun. 30, 1997, the contents of which are incorporated herein by reference.

BACKGROUND OF THE INVENTION

1. Field of the Invention

The present invention relates to a lamination type ceramic heater, which is applied to an oxygen sensor and the like.

2. Related Arts

An oxygen sensor element generally holds a heater for heating it to be an activation temperature. As the heater, recently, a plate-like lamination type heater has been widely used. The lamination type heater is typically composed of a ceramic heater substrate having heat and lead portions thereon and a ceramic cover plate disposed on the heater substrate to cover the heat and lead portions.

This type of ceramic heater is disclosed, for example in WO 94/14057 and JP-A-7-35723. In WO 94/14057, the ceramic heater has two heater layers electrically connected to one another in series. In JP-A-7-35723, a percentage of a short side with respect to a long side of the ceramic heater in cross section is fixed to be 75%–100%.

This ceramic heater is manufactured in the following way. First, two ceramic green sheets for the substrate and for the cover plate are prepared. After several heater patterns for the heat portion and the lead portion are printed on the ceramic green sheet for the substrate, the ceramic green sheet for the cover plate is laminated with the ceramic green sheet for the substrate, thereby forming a lamination body.

Next, the lamination body is baked. The baked lamination body is cut to be divided into several baked intermediate bodies, each of which has a corresponding one of the heater patterns thereon. Thereafter, conductive paste is printed on side surfaces of each of the intermediate bodies. The printed portions of the conductive paste become to serve as side electrodes by baking. Finally, lead wires are brazed to the side electrodes, so that the ceramic heater is finished.

However, in the above-mentioned method, cutting of the baked lamination body causes a plurality of micro-cracks in the lamination body, i.e., in the intermediate bodies. When the ceramic heater works, the ceramic heater has temperature distribution. For example, a surface temperature at a portion corresponding to the integrated heater portion is approximately 1000° C., and a surface temperature around the lead portions brazed to the side electrodes is approximately 400° C. This temperature distribution generates thermal stress in the ceramic heater, which can grow the above-mentioned micro-cracks so that the ceramic heater is damaged.

SUMMARY OF THE INVENTION

The present invention has been made in view of the above-mentioned problem. An object of the present invention is provide a method of manufacturing a lamination type ceramic heater without any micro-cracks therein.

According to the present invention, a lamination type, i.e., laminated, ceramic heater is manufactured in the following way. A conductive heater pattern having a terminal portion is formed on a first ceramic green sheet, and the first ceramic green sheet is laminated with a second ceramic green sheet to form a lamination body. Then, the lamination body is cut to form an intermediate body holding the heater pattern therein and having a side surface on which the terminal portion of the heater pattern is exposed. Then, the intermediate body is baked. That is, in the method of the present invention, after the intermediate body is provided by cutting the lamination body, the intermediate body is baked. No stress is applied to the intermediate body after it is baked. Even if the intermediate body has a micro-crack before it is baked, the micro crack can disappear when the intermediate body is baked. As a result, no micro-crack remains in the intermediate body, so that the ceramic heater can be provided without any micro-cracks therein.

To cut the lamination body, one groove may be formed on a surface of the lamination body, or two grooves may be formed on opposite surfaces of the lamination body, in the same plane. In this case, the lamination body is broken by applying stress on both sides of the groove.

BRIEF DESCRIPTION OF THE DRAWINGS

These and other objects and features of the present invention will become more readily apparent from a better understanding of the preferred embodiments described below with reference to the following drawings.

FIGS. 4A–4D are schematic views for explaining a method of manufacturing the ceramic heater in the first embodiment;

FIGS. 14A, 4B are schematic views for explaining a method of manufacturing a ceramic heater in a third preferred embodiment;

DETAILED DESCRIPTION OF THE PREFERRED EMBODIMENTS (First Embodiment)

Figure 1:
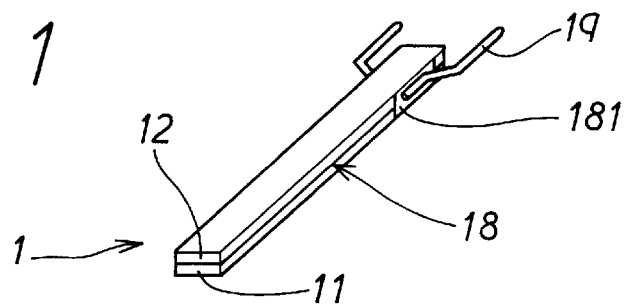
FIG. 1 is a perspective view showing a ceramic heater in a first preferred embodiment of the present invention.
Figure 2:
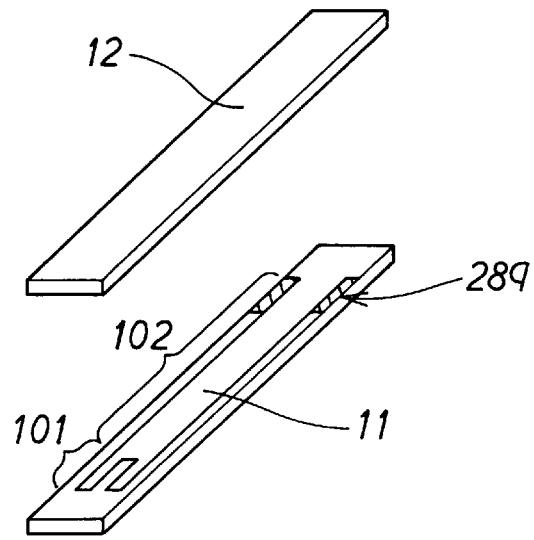
FIG. 2 is an exploded view showing the ceramic heater of FIG. 1.

A plate-like lamination type ceramic heater 1 in a first preferred embodiment is, as shown in FIGS. 1, 2, composed of a heater substrate 11 having a heater portion 101 and a pair of lead portions 102 thereon, a cover plate 12 disposed on the heater substrate 11 to cover the heater and lead portions 101, 102, and side electrodes 181 on side surfaces 18 of the ceramic heater 1. The side electrodes 181 electrically communicate with terminal portions 289 respectively provided on end portions of the lead portions 102, and with lead wires 19 connected to outside thereof.

When voltage is applied across the lead portions 102 through the lead wires 19 and the side electrodes 181, the heater portion 101 develops heat upon receiving electricity through the lead portions 102. The heater substrate 11 and the cover plate 12 are made of ceramic including alumina, silicon dioxide ($SiO_2$), and magnesium oxide (MgO). The heater portion 101 and the lead portions 102 are made of tungsten (W).

Figure 3:
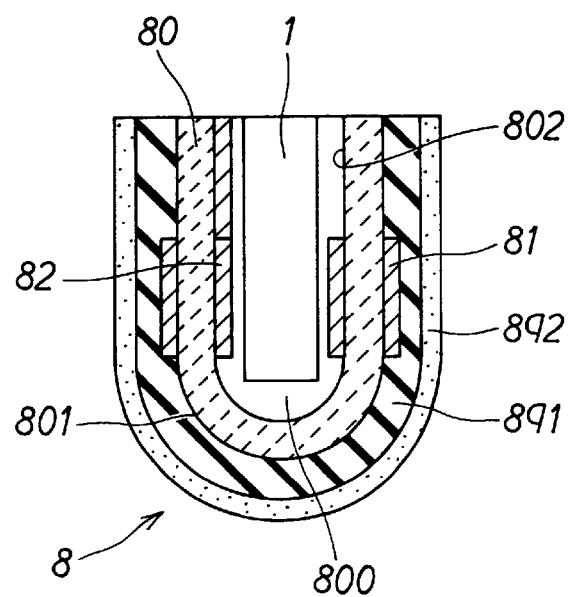
FIG. 3 is a schematic view showing the ceramic heater disposed in an oxygen sensor element.

The ceramic heater 1 in the first embodiment is applied to a cup-type oxygen sensor element 8 as shown in FIG. 3. Specifically, the oxygen sensor element 8 has a cup-type solid electrolyte body 80. The solid electrolyte body 80 has an air chamber 800 therein, and holds an outside electrode 81 on an outside surface 801 thereof and an inside electrode 82 on an inside surface 802 thereof within the air chamber 800. The outside electrode 81 is covered with a protection layer 891 for protecting the outside electrode 81 from contaminations contained in a measurement gas, and the protection layer 891 is further covered with a trap layer 892 for trapping the contaminations. The above-mentioned ceramic heater 1 is retained within the air chamber 800 of the solid electrolyte body 80 such that the integrated heater portion 101 of the ceramic heater 1 faces the inside electrode 82 of the oxygen, sensor element 8.

Next, a method of manufacturing the ceramic heater 1 will be explained with reference to FIGS. 4A–4D, and 5A, 5B.

First, slurry is formed from powders composed of 92 wt % alumina and 8 wt % $SiO_2$ and MgO. The slurry is formed into a sheet with 1.2 mm in thickness by a doctor blade method. Then, a square ceramic green sheet 21 for forming several substrates 11 and a square ceramic green sheet 22 for forming several cover plates 12, each size of which is 120 mm×120 mm, are formed from the sheet by a punching process. The ceramic green sheets 21, 22 may be formed by other processes such as an extruding process. In this embodiment, each number of the substrates 11 and the cover plates 12 provided from the green sheets 21, 22 is five.

Next, as shown in FIG. 4A, conductive paste containing metal such as W and molybdenum (Mo) as main components is printed on the ceramic green sheet 21 to form five heater patterns 20. One of the heater patterns 20 corresponds to the heat portion 101 and the lead portions 102 of the ceramic heater 1. In this case, the resistance of the heat portion 101 should be larger than that of the lead portions 102. Therefore, if necessary, this printing process may be performed twice using different kinds of conductive paste. Although the heater patterns 20 are schematically illustrated in FIG. 4A to be easily recognized, a practical size of each of the heater patterns 20 is smaller than that in FIG. 4A. Then, the ceramic green sheet 22 is laminated with the ceramic green sheet 21, thereby forming a lamination body 23 shown in FIG. 4B. Next, the lamination body 23 is cut along dashed lines in FIG. 4B, so that it is divided into five intermediate bodies 24. Edge portions 249 of the lamination body 23 are removed by this process. Each of the intermediate bodies 24 has a width of approximately 3.2 mm and a thickness of approximately 2 mm.

Figure 5A:
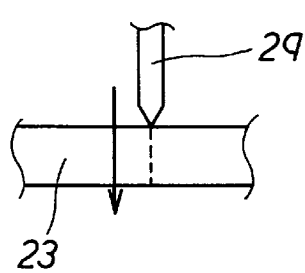
FIGS. 5A, 5B are schematic views for explaining a cutting process in the first embodiment.
Figure 5B:
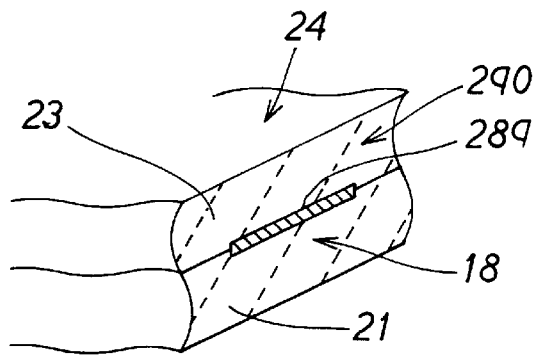

The cutting process is additionally explained with reference to FIGS. 5A, 5B. As shown in FIG. 5A, a blade 29 cuts the lamination body 23 along each of the dashed lines at a stretch while pushing it in a direction indicated with an arrow in FIG. 5A by a pushing cut method. As a result, the intermediate bodies 24 are provided. As shown in FIG. 5B, each of the intermediate bodies 24 has the side surfaces 18 entirely composed of cut surfaces 290 cut by the blade 29. The dashed lines cross the terminal portions 289 on the green sheet 21. Therefore, each of the side surfaces 18 of the intermediate bodies 24 exposes a corresponding one of the terminal portions 289 thereon.

Successively, as shown in FIG. 4C, conductive paste including W is printed on the side surfaces 18 of the intermediate bodies 24 to form printed portions 281 entirely covering the exposed terminal portions 289. The printed portions 281 are for the side electrodes 181. The conductive paste for the side electrodes 181 may be made of the same material as that for the heat patterns 20. Then, the intermediate bodies 24 are baked at a temperature in a range of 1400° C.–1600° C. Each size of the intermediate bodies 24 changes to 2.8 mm in width and 1.6 mm in thickness. The printed portions 281 become to serve as the side electrodes 181 during the baking process. The thus formed side electrodes 181. are plated with nickel (Ni). Then, after brazing filler metal such as Au—Cu brazing filler metal is disposed on the side electrodes 181, the lead wires 19 are brazed to the side electrodes 181 at a temperature in a range of 950° C.–1060° C. in a furnace as shown in FIG. 4D. In this way, the ceramic heater 1 is manufactured.

Next, features and effects in the first embodiment will be explained.

According to the method in the first embodiment, after the lamination body 23 is divided into the intermediate bodies 24, each of the intermediate bodies 24 is baked. No stress is applied to the intermediate bodies 24 after the intermediate bodies 24 are baked, so that micro-cracks are hardly produced in the intermediate bodies 24 after the baking process. Even if some micro-cracks are produced in the intermediate bodies 24 before the baking process, e.g., when the lamination body 23 is cut, the micro-cracks can disappear during the baking process. Especially, in this embodiment, the intermediate bodies 24 are made of alumina added with glass components ($SiO_2$ and MgO), the glass components in the intermediate bodies 24 changes from a solid phase to a liquid phase during the baking process. This baking mechanism facilitates the micro-cracks to disappear. Consequently, according to the method in this embodiment, the ceramic heater 1 can be manufactured without any micro-cracks therein. When the ceramic heater 1 works, even if thermal stress is generated in the ceramic heater 1 due to distribution of temperature, no breakage started from the micro-cracks occurs in the ceramics heater 1. The ceramic heater 1 can have high durability.

Other features and effects of the ceramic heater 1 will be explained in comparison with a ceramic heater manufactured by a conventional (comparative) method. The ceramic hater 1 manufactured by the above-mentioned method is referred to as sample 1. The ceramic heater manufactured by the following conventional method is referred to as sample C1.

Figure 6A:
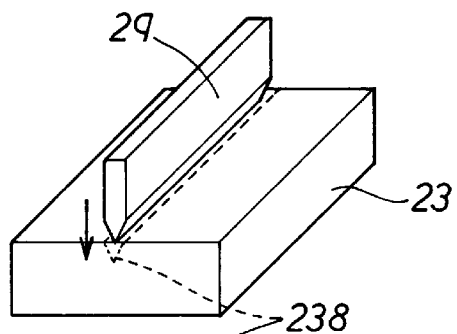
FIGS. 6A–6C are schematic views for explaining a comparative method of manufacturing a ceramic heater (sample C1), which is compared with the ceramic heater in the first embodiment.

The same parts and components as those for the ceramic heater 1 are described with the same reference numerals. In the conventional method, first, the lamination body 23 is produced substantially in the same manner as described above. Then, several grooves 238 are formed on the lamination body 23 along the dashed lines shown in FIG. 4B. Specifically, as shown in FIG. 6A, the grooves 238 are formed on the lamination body 23 by the blade 29. Then, the lamination body 23 is baked. The lamination body 23 after baked is referred to as a baked lamination body 239.

Figure 6B:
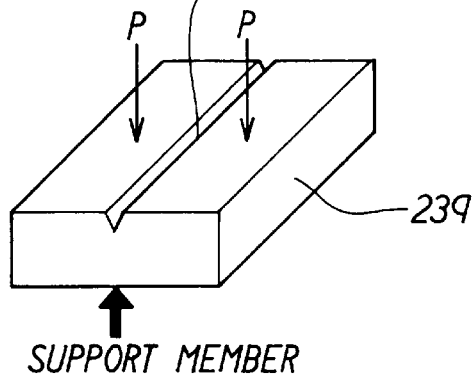

Next, as shown in FIG. 6B, in a state where the baked lamination body 239 is supported by a support member, stress P is applied to both sides of one of the grooves 238 to break the baked lamination body 239 along the one of the grooves 238. By repeating this process, five baked intermediate bodies 9 are provided. Thereafter, conductive paste capable of being baked at a temperature lower than that for the conductive paste used for the ceramic heater 1 is coated on side surfaces 180 of the baked intermediate bodies 9. Then, the coated conductive paste on the side surfaces 180 of the intermediate bodies 9 becomes to serve as side electrodes by baking. In this case, it is not necessary to bake the intermediate bodies 9 at a high temperature suitable for baking alumina, because the baking of alumina is already finished. Then, the lead wires are connected to the side electrodes as in the first embodiment, whereby the ceramic heater (sample C1) is provided.

Figure 7:
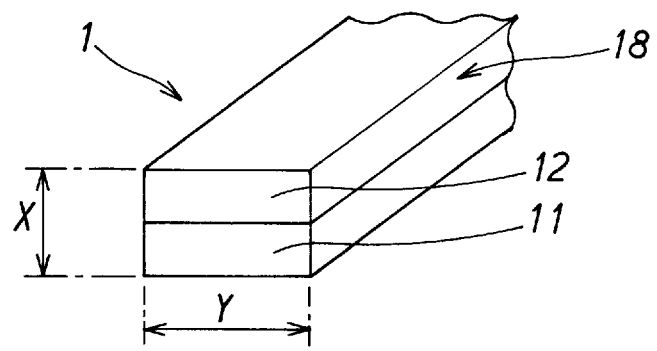
FIG. 7 is a perspective view partially showing the ceramic heater (sample 1) in the first embodiment.
Figure 8:
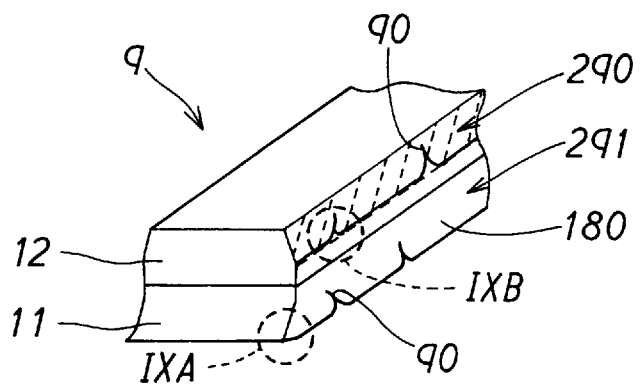
FIG. 8 is a perspective view partially showing sample C1.

Next, the side surfaces 18 of sample 1 and the side surfaces 180 of sample C1 are compared with one another. As shown in FIG. 7, the side surfaces 18 of sample 1 have no micro-cracks thereon. As opposed to this, as shown in FIG. 8, the side surfaces 180 of sample C1 have a plurality of micro-cracks 90 thereon. The reason is considered as follows.

Figure 6C:
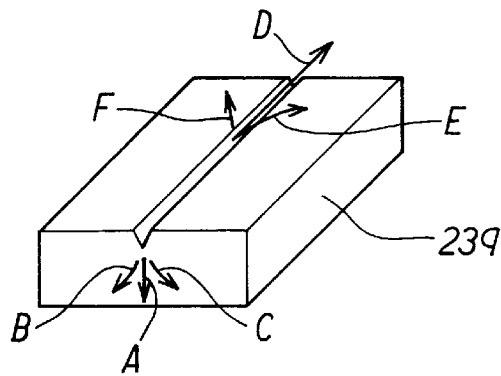

Each of the side surfaces 180 of sample C1 is composed of a cut surface 290 cut by the blade 29 for forming the grooves 238 and a breakage surface 291 formed by breakage of the baked lamination body 239. As described above referring to FIG. 6B, when the baked lamination body 239 is divided into the intermediate bodies 9, the stress P is applied to the lamination body 239 to break it. At that time, when each of the grooves 238 has a V-like shape with an acute angle, the breakage can progress in directions A and D shown in FIG. 6C. However, the surfaces of the grooves 238 on the baked lamination body 239 are curved by the baking process. Therefore, the breakage is liable to deviate in directions B or C, and E or F from the directions A, D.

Figure 9A:
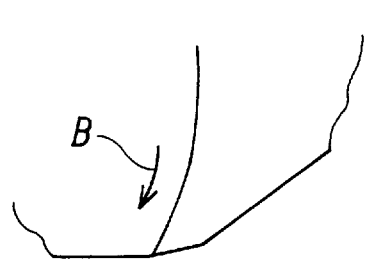
FIGS. 9A, 9B are schematic views respectively showing portion IXA and portion IXB of sample C1 shown in FIG. 8.
Figure 9B:
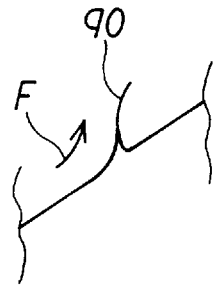

As shown in FIGS. 8, 9A, portion IXA of the side surfaces 180 is not liable to have micro-cracks thereon. This is because the breakage in direction A may deviate in either one of directions B, C; however, the direction B or C of the breakage is not changed until the lamination body 239 is completely divided by the breakage. As opposed to this, portion IXB shown in FIGS. 8, 9B is liable to have micro-cracks 90 thereon. This is because the breakage progressing in direction D is liable to change its direction on the way. For example, in FIG. 8, it is considered that the breakage progresses in direction D first, and changes the direction to be in direction E or F, and then changes the direction to be in direction D again. The micro-cracks 90 are produced where the direction of the breakage is changed as shown in FIG. 9B.

Figure 10:
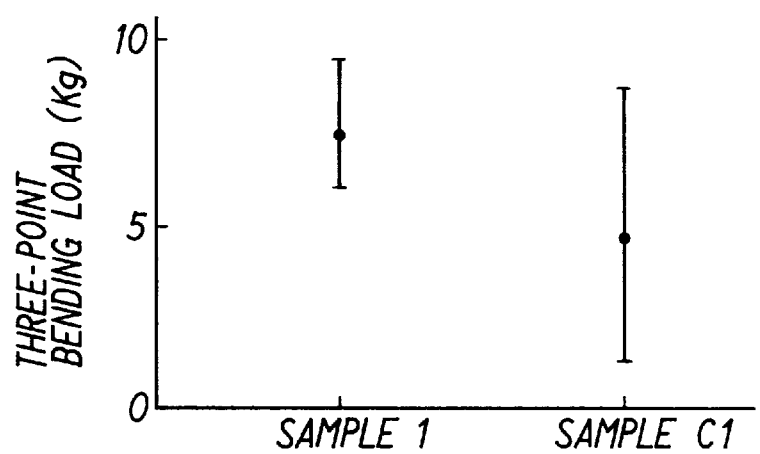
FIG. 10 is a graph showing three-point bending loads of sample 1 and sample C1.

Next, three-point bending loads of sample 1 and sample C1 were measured. To measure a three-point bending load of a sample, in a state where a surface of the sample is supported at two points, a load is applied to the other surface of the sample. In this case, a bending direction of the sample is approximately parallel to side surfaces thereof. The results of samples 1, C1 are shown in FIG. 10.

The three-point bending loads of sample 1 of the first embodiment have an average larger than that of sample C1 and variation smaller than that of sample C1. By observing the broken samples 1, C1 with a scanning electron microscope (SEM), it was found that the breakage of sample 1 started from the central portion of the surface opposite to the other surface to which the load was applied. It was further found that the breakage of sample C1 started from the micro-cracks 90 on the side surfaces 180. This difference between sample 1 and sample C1 may cause the difference in the three-point loads therebetween. Accordingly, it is confirmed that, at a room temperature at which thermal stress is not produced, breakage strength of the ceramic heater 1 (sample 1) is significantly improved as compared with sample C1 manufactured by the conventional method.

Next, operational durability of each of samples 1, C1 was examined by a durability test. Specifically, voltage was applied to each of the samples 1, C1 until the surface temperature of each of samples 1, C1 became 1000° C., and then samples 1, C1 were left at 1000° C. The numbers of samples 1, C1 examined by the test were respectively thirty. When a rising rate of a value of resistance of a sample exceeded 20% with respect to its initial value of resistance as the durability test started, the sample was regarded as an operational defective.

Figure 11:
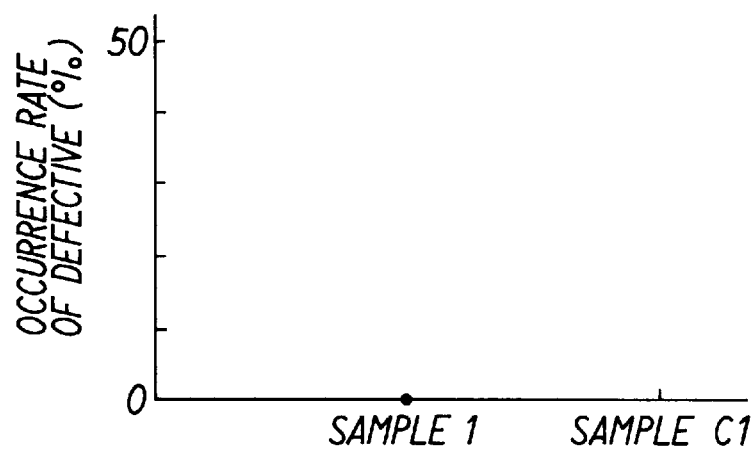
FIG. 11 is a graph showing occurrence rates of defective of sample 1 and sample C1.

FIG. 11 shows occurrence rates of operational defectives of samples 1, C1 after 1000 hours from the start of the durability test at 1000° C. Sample C1 had three defectives in the thirty samples. It is deduced that the micro-cracks progress due to thermal stress so that the heat portion and the lead portions integrated in sample C1 are oxidized to increase the value of resistance thereof. Sample 1 did not have any defective. Accordingly, it is confirmed that the ceramics heater 1 (sample 1) of the first embodiment has high durability at a high temperature at which thermal stress is generated.

Further, a plurality of ceramic heaters 1 (sample 1) having different thicknesses X and different widths Y (see FIG. 7) were manufactured, and they were examined those assembling defects. That is, when each of the ceramic heaters 1 was put in the oxygen sensor element 8 as shown in FIG. 3, it was examined whether the ceramic heater 1 was broken or not. The assembling process was ordinarily performed. The results are shown in FIG. 12.

Figure 12:
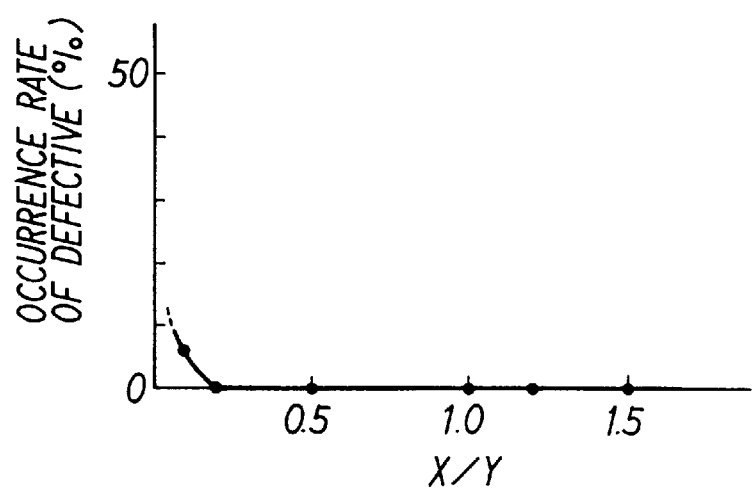
FIG. 12 is a graph showing a relationship between ratio X/Y in size of the ceramic heater shown FIG. 7 and occurrence rate of defective by an assembling process.

As understood from FIG. 12, when ratio X/Y is smaller than 0.2, the ceramic heater 1 may be broken during the assembling process. When ratio X/Y is larger than 0.2, the ceramic heater 1 is not broken during the assembling. Conventionally, ratio X/Y of the ceramic heater cannot be sufficiently decreased, because the conventional ceramic heater has a plurality of micro-cracks therein, which decreases the strength of the ceramic heater. According to the method of the present invention providing no microcracks in the ceramic heater 1, the ceramic heater 1 can be formed with a thickness thinner than that of a conventional one. In other words, according to the method of the present invention, it is possible for the ceramic heater 1 to have ratio X/Y with a wide range in a practical use. That is, the ceramic heater 1 has flexibility in design. However, it is undesirable for the ceramic heater 1 to have ratio X/Y exceeding 1.5, since it becomes difficult to print the conductive paste for the heater pattern 20 on the ceramic heater 1.

(Second Embodiment)

Figure 13A:
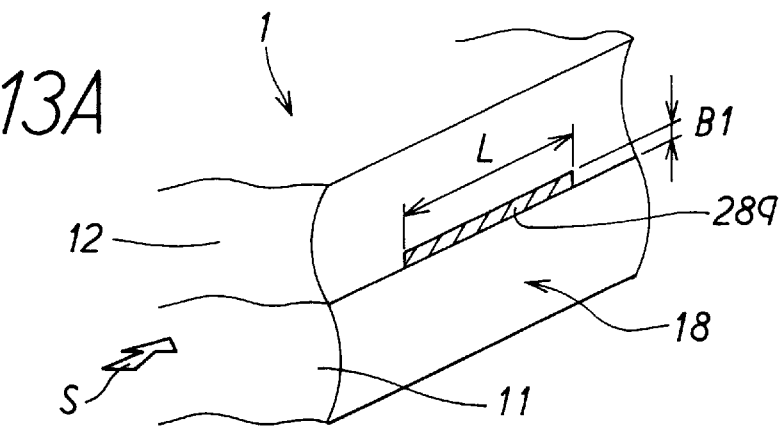
FIG. 13A is a schematic view partially showing a side surface of a ceramic heater in a second preferred embodiment.
Figure 13B:
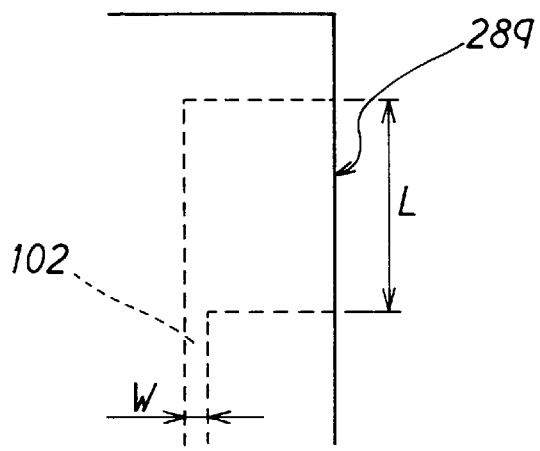
FIG. 13B is s plan view partially showing the ceramic heater in the second embodiment.

In a second preferred embodiment, as shown in FIG. 13B, the heater pattern 20 with constant thickness A1 is formed to have the lead portions 102 with width W and the terminal portions 289 with length L. The terminal portions 289 are exposed on the side surfaces 18 of the ceramic heater 1 as shown in FIG. 13A, and the side electrodes respectively cover the exposed terminal portions 289 as in the first embodiment.

Figure 13C:
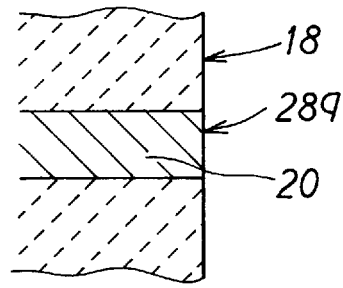
FIG. 13C is a cross-sectional view partially showing an ideal state of a terminal portion of the ceramic heater in the second embodiment.
Figure 13D:
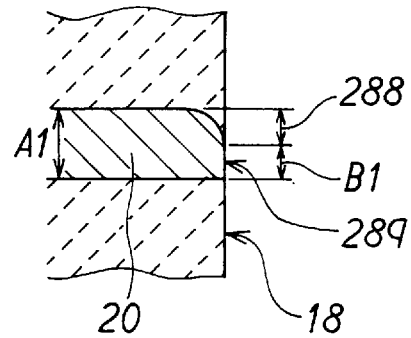
FIG. 13D is a cross-sectional view partially showing a state of the terminal portion having a deformed portion in the second embodiment.

Each of the side surfaces 18 is composed of a cut surface cut by the blade as in the first embodiment. A cross-sectional view of one of the terminal portions 289 observed in a direction indicated with arrow S in FIG. 13A is shown in FIGS. 13C, 13D. FIG. 13C shows an ideal shape of the terminal portion 289; however, the edge portion of the terminal portion 289 is easily deformed by stress applied thereto during the cutting process as shown in FIG. 13D. The deformed portion of the terminal portion 289 is indicated with reference numeral 288. When the terminal portion 289 is deformed as shown in FIG. 13D, the thickness of the terminal portion 289 exposed on one of the side surfaces 18 is reduced to be B1 as shown in FIG. 13A.

In the second embodiment, assuming that the terminal portion 289 has the deformed portion 288, the ceramic heater 1 is designed to satisfy a relationship of L≧(A1/B1)× W. The other features are the same as those in the first embodiment.

In the second embodiment, the area of the terminal portion 289 exposed on the side surface 18 is reduced due to the deformed portion 288. If the ceramic heater 1 has a relationship of L<(A1/B1)×W, supply of electricity to the ceramic heater 1 raises the value of resistance of the exposed terminal portion 289. As a result, the exposed terminal portion 289 develops heat. As opposed to this, in the second embodiment, because the heater pattern 20 is formed to satisfy the relationship of L≧(A1/B1)×W, the value of resistance of the exposed terminal portion 289 is smaller than that of the lead portion, so that increase in resistance of the exposed terminal portion 289 can be prevented. As a result, heat is hardly generated from the terminal portion 289. The other features and effects are the same as those in the first embodiment.

(Third Embodiment)

Figure 14A:
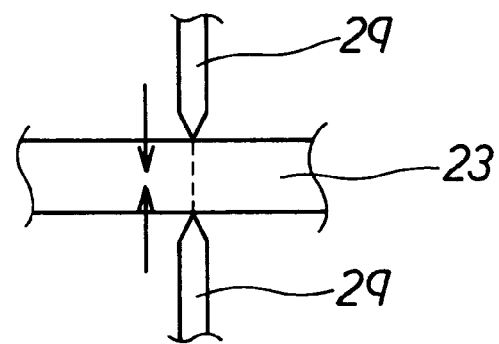

In a third embodiment, the lamination body 23 is cut by using a pair of grooves formed on the lamination body 23. Specifically, two blades 29 are set on both surfaces of the lamination body 23 to push it in directions indicated with arrows in FIG. 14A. Then, the blades 29 are moved to form the pair of grooves on the both surfaces of the lamination body 23. Each of the grooves has 0.3 mm in width and 0.7 mm in depth. Then, stress is applied to both sides of one of the grooves as explained in the first embodiment referring to FIG. 6B to break the lamination body 23. As a result, an intermediate body 324 is provided with the side surface 181 composed of cut surfaces 290 cut by the blades 29 for forming the grooves and a breakage surface 291. The other features are the same as those in the first embodiment.

According to the third embodiment, the intermediate body 324 can be formed without receiving large force from the blade 29. Therefore, the terminal portion 289 can be prevented from being largely deformed by the cutting process. Because the two grooves are formed on the both surfaces of the lamination body 23, each depth of the grooves can be reduced. Therefore, the lamination body 23 is not largely deformed and collapsed by the formation of the grooves. The desirable width of each of the grooves is in a range of 0.2 mm–0.9 mm, and the desirable depth of each of the grooves is in a range of 0.4 mm–0.9 mm. When. the width of each of the grooves is smaller than 0.2 mm, the progress of the breakage may be unsteady. When the width is larger than 0.9 mm, the terminal portion 289 exposed on the side surface 181 may be deformed. When the depth of each of the grooves is smaller than 0.4 mm, the progress of the breakage may be unsteady. When the depth is larger than 0.9 mm, the terminal portion 289 exposed on the side surface 181 may be deformed.

Figure 14B:
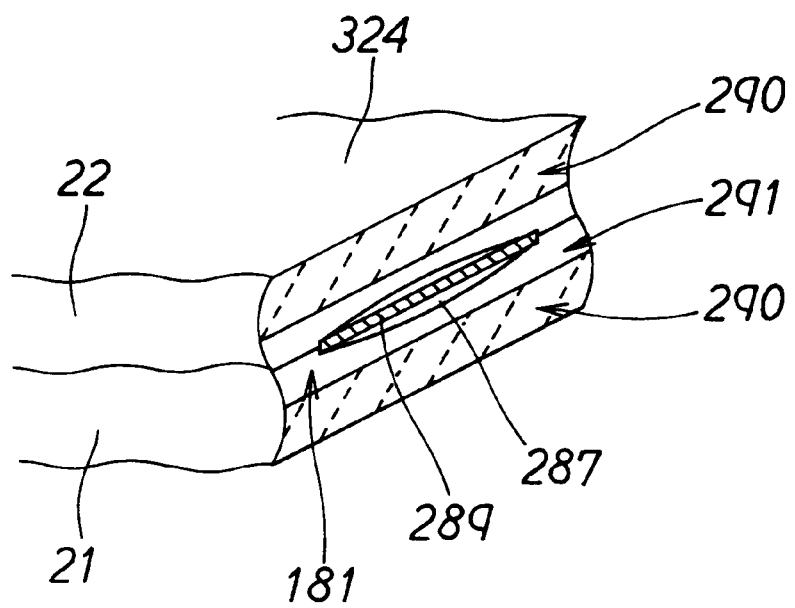

The lamination body 23 is broken by tensile stress applied to the both sides of the one of the grooves. By the breakage, as shown in FIG. 14B, the ceramic green sheets 21, 22 are slightly separated from one another, so that an opening portion 287 is formed around the exposed terminal portion 289 between the ceramic green sheets 21, 22. By the opening portion 287, an exposed area of the terminal portion 287 is increased. As a result, conductivity of the side electrode formed on the terminal portion 289 is improved. The side surface 181 is composed of the cut surfaces 290 and the breakage surface 291. The cut surfaces 290 are smooth, while the breakage surface 291 is rough. The roughness of the breakage surface 291 remains after the intermediate body 324 is baked so that it improves adhesive strength between the side electrode and the side surface 181. The grooves can be formed only on one of the surfaces of the lamination body 23. The other features and effects are the same as those in the first embodiment.

(Fourth Embodiment)

In a fourth preferred embodiment, a ceramic heater has two layers of heater patterns electrically connected to one another in parallel. In a method of manufacturing the ceramic heater, two ceramic green sheets respectively having the heater patterns thereon are laminated with one another and another ceramic green sheet for the cover plate is laminated with the laminated two green sheets, thereby forming a lamination body. Then, the lamination body is cut to be divided into several intermediate bodies.

Each of the intermediate bodies has side surfaces, and each of the side surfaces exposes a corresponding terminal portion composed of the two layers of the heater patterns. Printed portions for side electrodes are printed on the side surfaces of the intermediate bodies to cover the exposed terminal portions. Then, each of the intermediate bodies is baked so that the printed portions can serve as the side electrodes, thereby forming the ceramic heater. The temperature of the ceramic heater in the fourth embodiment can be raised with low power. The other features and effects are the same as those in the first embodiment.

(Fifth Embodiment)

Figure 15A:
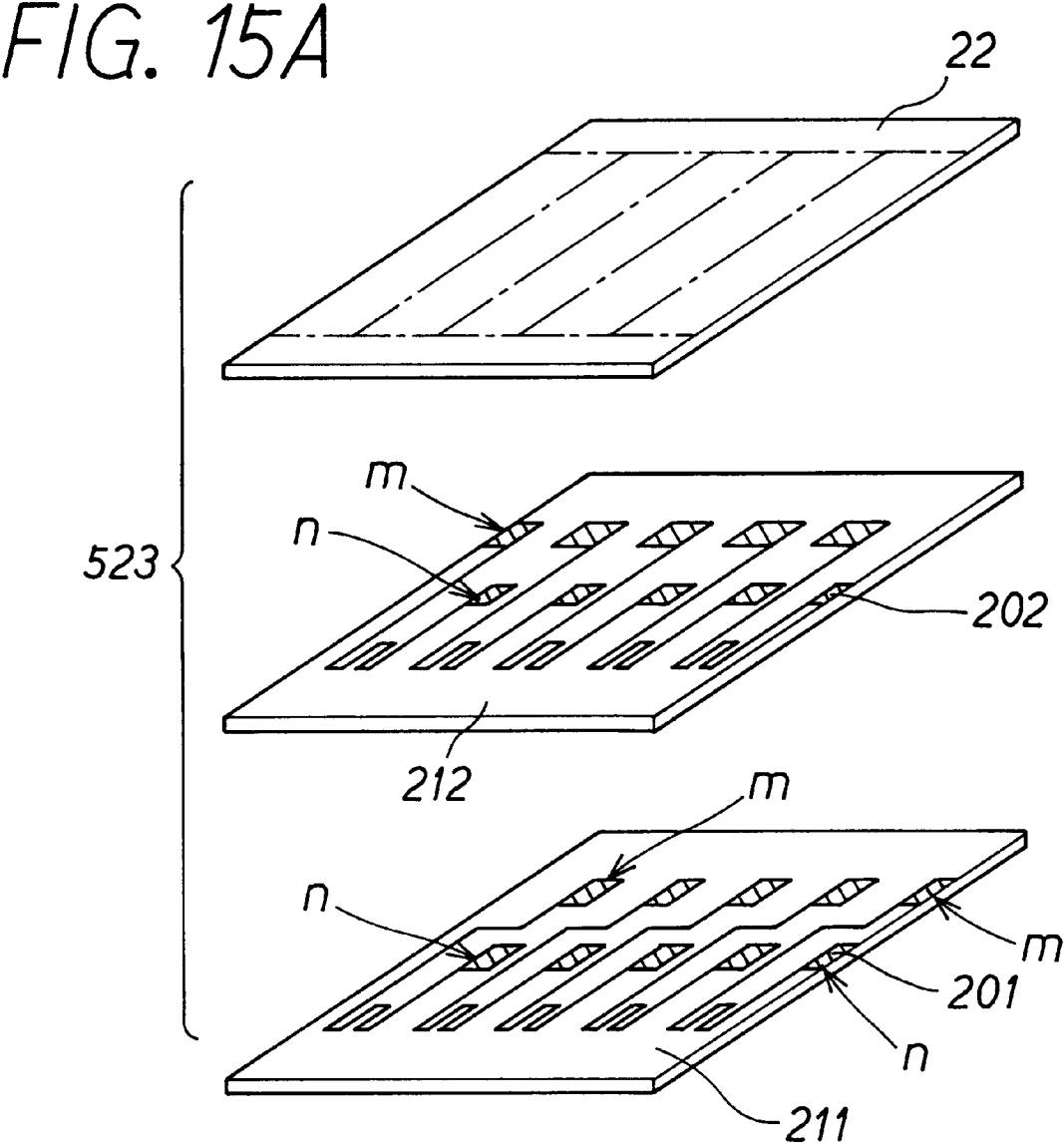
FIGS. 15A, 15B are schematic views for explaining a method of manufacturing a ceramic heater in a fifth preferred embodiment.
Figure 15B:
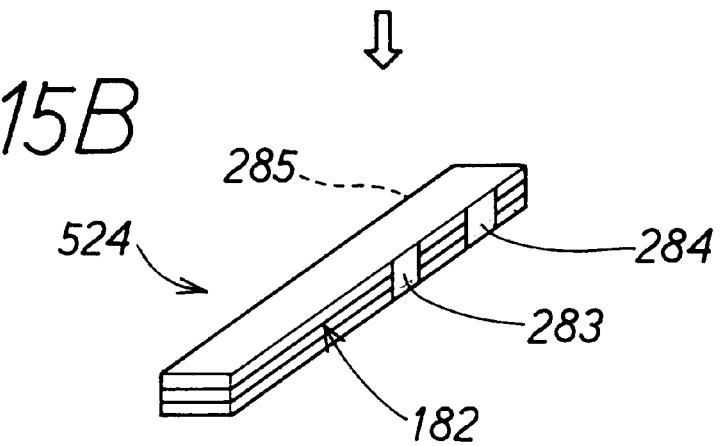

A ceramic heater in a fifth preferred embodiment has two layers of heater patterns, which are electrically connected to one another in series. In a method of forming the ceramic heater, as shown in FIG. 15A, two ceramic green sheets 211, 212, respectively having the heater patterns 201, 202 thereon and a ceramic green sheet 22 for the cover plate are prepared. The ceramic green sheets 211, 212, 22 are laminated with one another, thereby forming the lamination body 523. An intermediate body 524 shown in FIG. 15B is formed by cutting the lamination body 523.

The intermediate body 524 has three terminal portions exposed side surfaces 182 thereof. Two of the exposed terminal portions are parts of m portions of the heater patterns 201, 202 shown in FIG. 15A, and the other one of the exposed terminal portions is part of n portions of the heater patterns 201, 202. Then, as shown in FIG. 15B, printed portions 283, 284, 285 are disposed on the three exposed terminal portions. The printed portions 283, 284, 285 become side electrodes by baking the intermediate body 524. By bonding lead wires to the side electrodes, a ceramic heater is provided.

In the ceramic heater according to the fifth embodiment, the two layers of the heater pattern are electrically connected to one another without any through holes. Therefore, the manufacturing cost of the ceramic heater is low. In addition, there is no wire breakage defective in the through holes caused by a difference in coefficient of contraction between the ceramic green sheets and an conductive member filling the through holes. The other features and effects are the same as those in the first embodiment.

(Sixth Embodiment)

Figure 16:
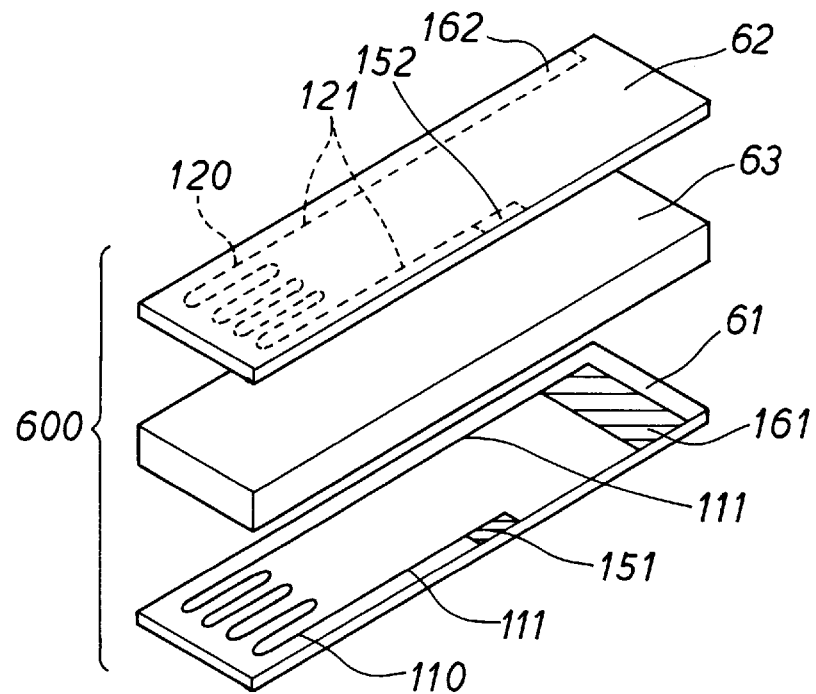
FIG. 16 is an exploded perspective view showing a ceramic heater in a sixth preferred embodiment.
Figure 17:
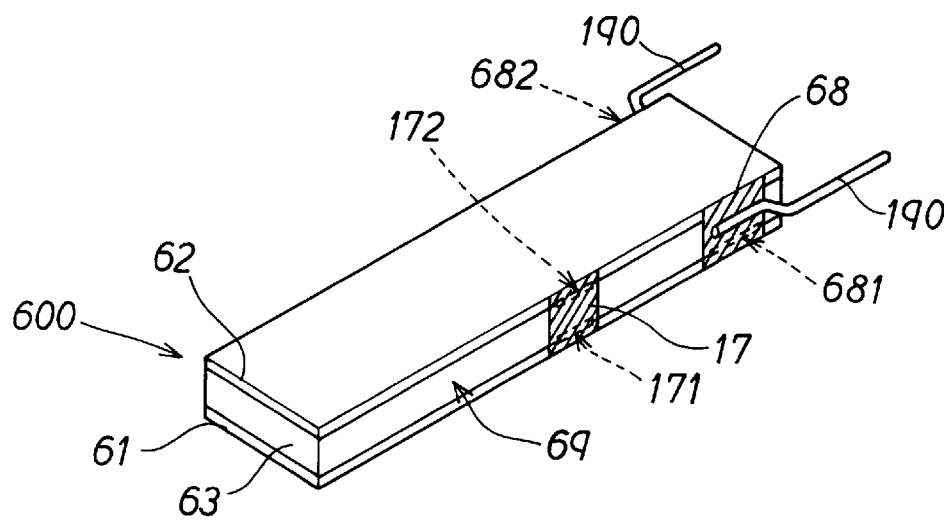
FIG. 17 is a perspective view showing the ceramic heater in the sixth embodiment.

A ceramic heater 600 in a sixth preferred embodiment is, as shown in FIGS. 16, 17, composed of two heater substrates 61, 62 and an insulating substrate 63 interposed between the heater substrates 61, 62. Each of the heater substrates 61, 62 has a heat layer 110 or 120 and a lead layer 111 or 121 for supplying electricity to the heat layer 110 or 120. The heat substrates 61, 62 are overlapped with one another such that the heater layers 110, 120 face one another through the insulating substrate 63.

The lead layers 111, 121 respectively have terminal portions 151, 161, 152, 162 at ends portions thereof. The terminal portions 151, 152 respectively have exposed portions 171, 172 exposed on one of the side surfaces 69 of the ceramic heater 600. The exposed portion 171 of the terminal portion 151 is electrically connected to the exposed portion 172 of the terminal portion 152 through a connecting conductive portion 17 disposed on the one of the side surfaces 69. Accordingly, the two heat layers 110, 120 are electrically connected to in series. The terminal portions 161, 162 also have exposed portions 681, 682 exposed on the side surfaces 69, and lead wire connecting conductive portions 68 are formed on the side surfaces 69 to respectively cover the exposed portions 681, 682 of the terminal portions 161, 162. Further, lead wires 190 are respectively connected to the lead wire connecting conductive portions 68 so that it supplies electricity to the heat layers 110, 120.

Next, a method of manufacturing the ceramic heater 600 will be explained. First, slurry including source powder composed of 92 wt % $Al_2O_3$ and 8 wt % $SiO_2$ and MgO is formed into a sheet with 0.35 mm in thickness by a doctor blade method. Then, eight square green sheets are formed from the sheet by a punching-press process. Each size of the square green sheets is approximately 120 mm×120 mm. The square green sheets may be formed by other processes such as an extruding process.

Next, powder composed of W and rhenium (Re) having a ratio in weight of 80/20, binder, and plasticizer are mixed by a three-roll mill apparatus, thereby forming conductive paste. The conductive paste is screen-printed on two of the green sheets to respectively form several heater patterns 611, 612 as shown in FIG. 3A. The heater patterns 611, 612 may be formed by a pad printing-method. The two green sheets 610, 620 are for the heater substrates 61, 62. Each of the heater patterns 611, 612 corresponds to the heat layer and the lead layer of one of the heater substrates 61, 62 of the ceramic heater 600. In this method, five ceramic heaters are manufactured at a time.

Six of the above-mentioned green sheets are stacked and fixed to one another by pressure to form a member 630 for the insulating substrate 63. The member 630 can be formed by an extruding method. Then, the two green sheets 610, 620 for the heater substrates 61, 62 are stacked with and attached to the member 630 by pressure such that the heater patterns 611, 612 of the green sheets 610, 620 abut the member 630 interposed therebetween. As a result, a lamination body is provided. Then, the lamination body is dried.

Figure 18:
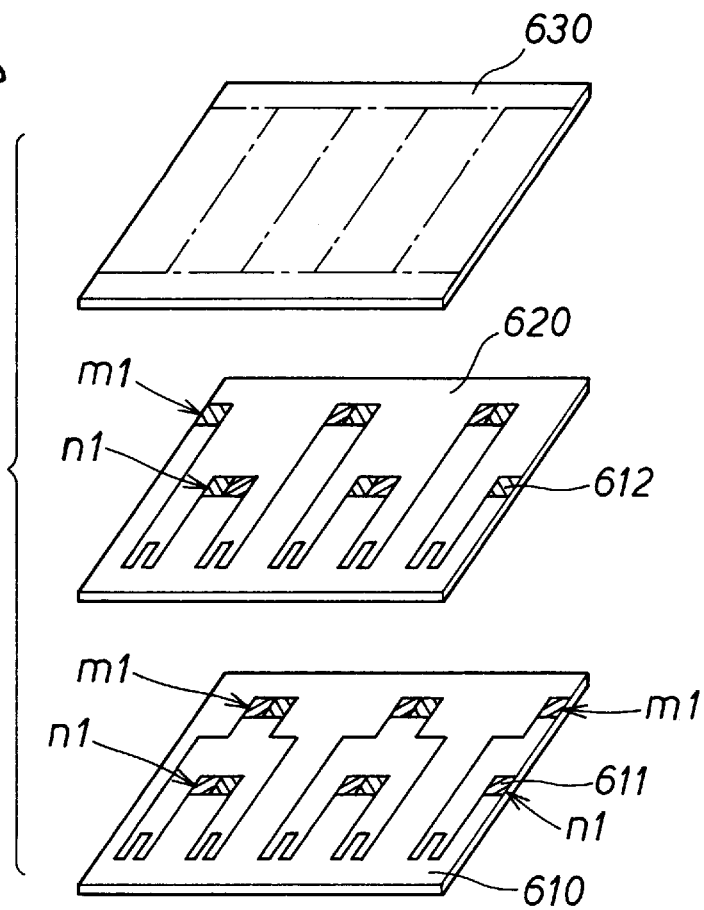
FIGS. 18, 19 are schematic views for explaining a method of manufacturing ceramic heater in the sixth embodiment.
Figure 19:
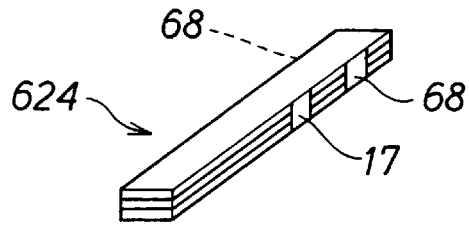

Successively, the lamination body is cut along dashed lines shown in FIG. 18, thereby forming intermediate bodies 624, one of which is shown in FIG. 19. The intermediate body 624 has side surfaces on which the terminal portions 151, 152, 161, 162 are respectively exposed as the exposed portions 171, 172, 681, 682. The exposed portions 171, 172, 681, 682 are covered with conductive paste by a printing method, so that printed portions are disposed on the exposed portions 171, 172, 681, 682.

Then, the intermediate body 624 is baked at 1580° C. within a reduced atmosphere furnace including nitrogen and hydrogen. The printed portions are baked during the baking process to serve as the connecting conductive portion 17 and the lead wire connecting conductive portions 68. In this embodiment, because the conductive paste for the heat layer and the lead layer includes W, the intermediate body 624 is baked in a reduced atmosphere; however when the material for the heat layer and the lead layer is made of platinum (Pt) or the like, the intermediate body 24 may be baked in an atmospheric air.

Then, the connecting conductive portion 17 and the lead wire connecting conductive portions 68 are plated with nickel (Ni) by an electroless plating process. The lead wires 190 are connected to the lead wire connecting conductive portions 68 through brazing filler metal including copper. Then, the lead wire connecting conductive portions 68 are plated with Ni again. Thus, the ceramic heater 600 in the sixth embodiment is manufactured.

Next, features and effects in the sixth embodiment will be described. In the ceramic heater 600, the terminal portions 151, 152 of the lead layers 111, 121 are connected to one another in series via the connecting conductive portion 17. Accordingly, the heat layers 110, 120 on the heat substrates 61, 62 are electrically connected in series without any through holes. In this embodiment, the thickness of the connecting conductive portion 17 is 0.01 mm–0.02 mm. Generally, as the thickness of the conductive portion becomes thin, it becomes difficult for the conductive portion to have breakage thereof. Therefore, the connecting conductive portion 17 hardly has cracks and breakages, resulting in high reliability of the ceramic heater 600. In addition, the connecting conductive portion 17 is easily formed by the printing process. Because connecting between the terminal portions 151, 152 of the lead layers 111, 121 is assured by the connecting conductive portion 17 having a sufficient width, even if the heater substrates 61, 62 slightly deviate from one another when overlapped, the terminal portions 151, 152 can be connected to each other through the connecting conductive portion 17. The ceramic heater 600 is not liable to have a defect caused by positioning deviation thereof. In this way, the ceramic heater 600 is easily manufactured without any defectives at low cost.

In the sixth embodiment, although the ceramic heater 600 includes the two heater substrates 61, 62, the ceramic heater may include more than three heater substrates. The heater substrates may be stacked with one another by using adhesives. The other features and effects are the same as those in the first embodiment.

(Seventh Embodiment)

Figure 20:
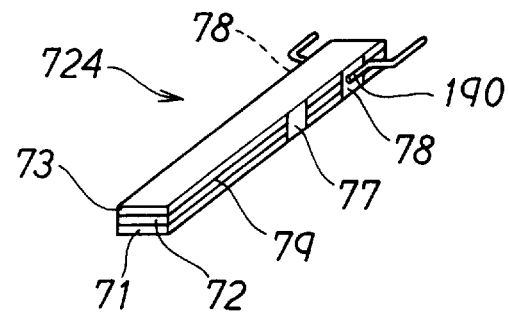
FIG. 20 is a perspective view showing a ceramic heater in a seventh preferred embodiment.

A ceramic heater in a seventh preferred embodiment is composed of two heater substrates 71, 72 and a cover plate 73 covering the heater substrates 71, 72 as shown in FIG. 20.

Herebelow, a method of manufacturing the ceramic heater will be explained with reference to FIG. 18. First, the green sheets 610, 620, and the member 630 formed from six green sheets are prepared substantially in the same manner as in the sixth embodiment. The green sheets 610, 620 are for the heater substrates 71, 72, and the member 630 is for the cover plate 73. Then, in the seventh embodiment, as shown FIG. 18, the green sheet 63 is disposed on the green sheets 61, 62 laminated with one another, thereby forming a lamination body. That is, the laminating order of the green sheets 610, 620, 630 is different from that in the sixth embodiment.

Next, the lamination body is cut along the dashed lines shown in FIG. 18, thereby forming five intermediate bodies 724, one of which is schematically shown in FIG. 20. The intermediate body 724 has side surfaces 79 on which nl printed portions and ml printed portions of the heat patterns 611, 612 shown in FIG. 18 are exposed as exposed portions. Then, conductive paste is printed on the side surfaces 79 of the intermediate body 724 to cover the exposed portions as a connecting conductive portion 77 and as lead wire connecting conductive portions 78 shown in FIG. 20. After the conductive paste is printed, the intermediate body 724 is baked, and then, the lead wires 190 are connected to the lead wire connecting conductive portions 78. In this way, the ceramic heater in the seventh embodiment is manufactured. The seventh embodiment can provide substantially the same effects as those in the sixth embodiment.

(Eighth Embodiment)

Figure 21:
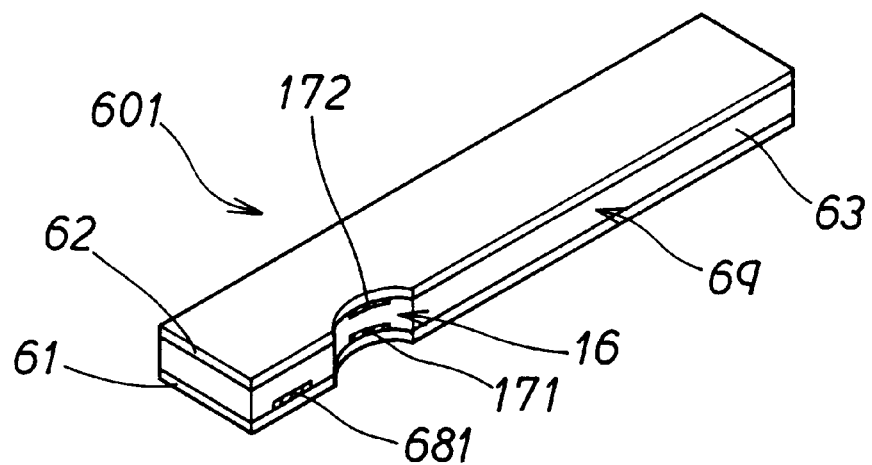
FIG. 21 is a perspective view showing a recess formed on a side surface of a ceramic heater in an eighth preferred embodiment.
Figure 22:
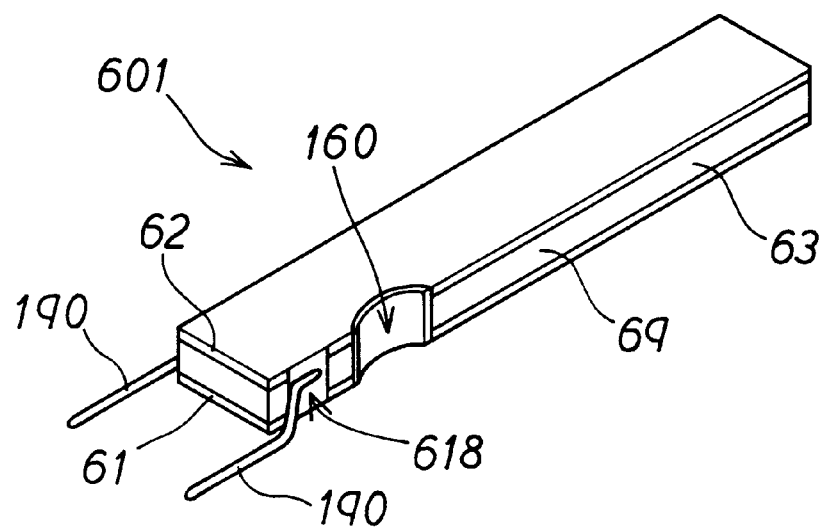
FIG. 22 is a perspective view showing the ceramic heater in the eighth embodiment.

A ceramic heater 601 in a eighth preferred embodiment is composed of the heater substrates 610, 620 and the insulating substrate 630 interposed between the heater substrates 610, 620 as in the sixth embodiment. The difference between the ceramic heaters 600, 601 of the sixth and eighth embodiments is that the ceramic heater 601 of the eighth embodiment has a recess 16 on one of the side surfaces 69 thereof as shown in FIG. 21. The exposed portions 171, 172 of the terminal portions 151, 152 are exposed on a surface of the recess 16. A connecting conductive portion 160 of the ceramic heater 601 is disposed on the surface of the recess to cover the exposed portions 171, 172 as shown in FIG. 22. The recess 16 has a semicircular shape in cross section.

A method of manufacturing the ceramic heater 601 is as follows. First, the green sheets 610, 620 on which the heater patterns 611, 612 are printed and the member 630 formed from six green sheets are prepared substantially in the same manner as in the sixth embodiment. Then, the green sheets 610, 620 and the member 630 are stacked with and fixed to one another by pressure such that the heater patterns 611, 612 abut the member 630 interposed therebetween, thereby forming a lamination body 823.

Figure 23A:
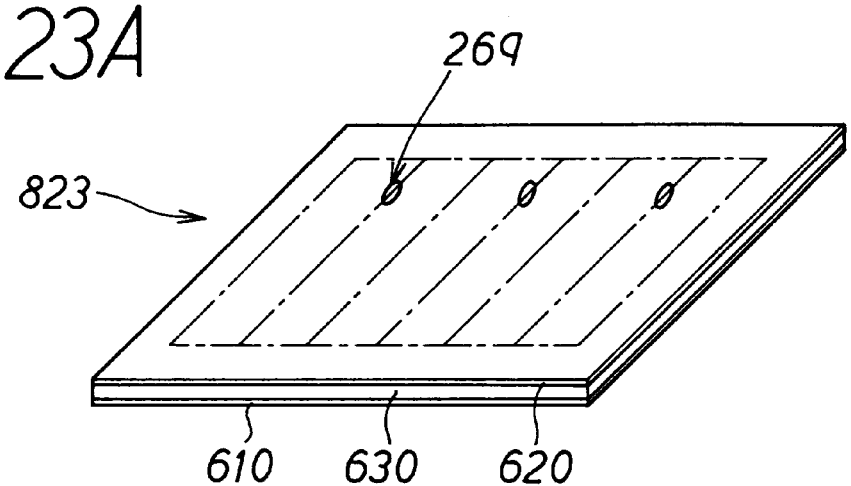
FIGS. 23A–23C schematic views for explaining a method of manufacturing the ceramic heater in the eighth embodiment.
Figure 23B:
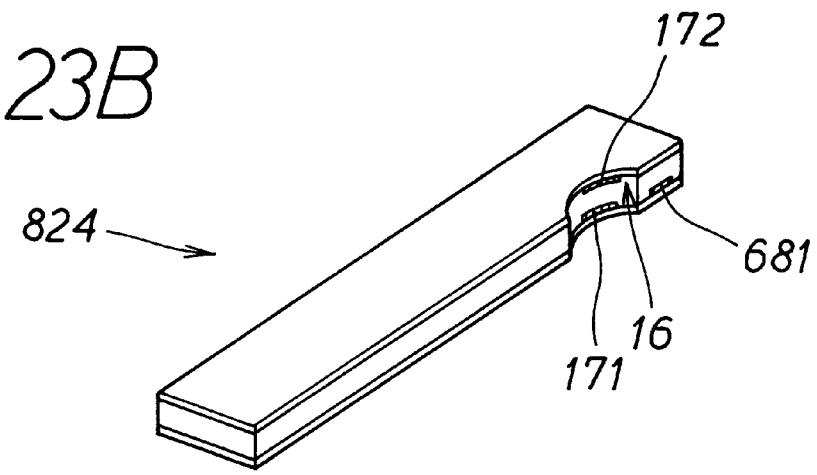
Figure 23C:
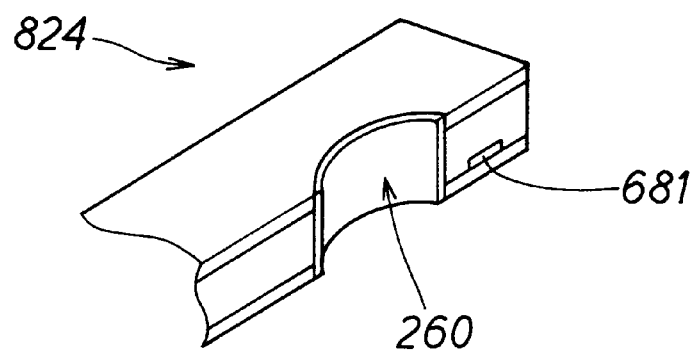

Next, as shown in FIG. 23A, through holes 269 for the recess 16 are formed with a specific shape in the lamination body 823 by a punching machine. After the through holes 269 are formed, the lamination body 823 is cut along dashed lines shown in FIG. 23A, thereby forming several intermediate bodies 824. One of the intermediate bodies 824 is shown in FIG. 23B. Then, as shown in FIG. 23C, a printed portion 260 is formed on the surface of the recess 16 of the intermediate body 824 by a pad printing method. By baking the intermediate body 824 as in the sixth embodiment, the printed portion 260 becomes to serve as the connecting conductive portion 160. Finally, the lead wires 190 are connected to the ceramic heater 601.

In the eighth embodiment, the connecting conductive portion 160 caves in from one of the side surfaces 618 of the ceramic heater 601. Therefore, the connecting conductive portion 160 is not damaged by stationary parts such as a holder. In addition, the area of the connecting conductive portion 160 is increased, so that adhesive strength between th.e exposed portions 171, 172 and the connecting conductive portion 160 is enhanced. The other features and effects are the same as those in the sixth embodiment.

While the present invention has been shown and described with reference to the foregoing preferred embodiment, it will be apparent to those skilled in the art that changes in form and detail may be made therein without departing from the scope of the invention as defined in the appended claims.

What is claimed is:

1. A method of manufacturing a laminated ceramic heater, comprising steps of:

preparing first and second ceramic green sheets;

forming a heater pattern on the first ceramic green sheet, the heater pattern having a terminal portion;

laminating the first and second ceramic green sheets with the heater pattern interposed between the first and second ceramic green sheets to form a lamination body;

cutting the lamination body to form an intermediate body holding the heater pattern therein and having a side surface on which the terminal portion of the heater pattern is exposed, said cutting step including cutting the lamination body through at least a portion of the terminal portion, thereby to form a cut surface of the terminal portion, whereby said cut surface of the terminal portion is exposed at said side surface of the terminal body; and baking the intermediate body.

2. The method of claim 1, wherein the lamination body is cut with a cutting device that is pushed from above.

3. The method of claim 1, wherein the step of cutting the lamination body comprises steps of:

forming a groove on a surface of the lamination body; and applying stress to the lamination body on both sides of the groove.

4. The method of claim 3, wherein in the step of forming the groove, two grooves are respectively formed on opposite surfaces of the lamination body, in the same plane.

5. The method of claim 1, wherein the heater pattern has a heat portion and a lead portion.

6. The method of claim 5, wherein the heater pattern is formed to satisfy a relationship of $L \geq (A1/B1) \times W$, wherein A1 is a thickness of the heater pattern interposed between the first and second ceramic green sheets, B1 is a thickness of the terminal portion exposed on the side surface of the intermediate body, L is a length of the terminal portion exposed on the side surface of the intermediate body, and W is a width of the lead portion of the heater pattern.

7. The method of claim 1, further comprising a step of printing a side electrode on the side surface of the intermediate body to cover the terminal portion exposed on the side surface, before the step of baking the intermediate body.

8. The method of claim 1, further comprising a step of preparing a third ceramic green sheet before the step of forming the heater pattern, wherein:

in the step of forming the heater pattern, a first heater pattern is formed on the first ceramic green sheet with a first terminal portion and a second heater pattern is formed on the third ceramic green sheet with a second terminal portion;

in the step of laminating the first and second ceramic green sheets, the third ceramic green sheet is further laminated with the first and second ceramic green sheets to form the lamination body; and the intermediate body formed by cutting the lamination body has the side surface on which both of the first and second terminal portions are exposed.

9. The method of claim 8, further comprising a step of forming a conductive member on the side surface of the intermediate body to electrically connect the first and second terminal portions in series.

10. The method of claim 8, wherein the side surface of the intermediate body has a recess, and the first and second terminal portions are exposed on the recess.

11. The method of claim 8, wherein the second ceramic green sheet is disposed between the first and third ceramic green sheets in the lamination body.

12. The method of claim 8, wherein one of the first and third ceramic green sheets is disposed between the other of the first and third ceramic green sheets, and the second ceramic green sheet in the lamination body.

13. A method of manufacturing a laminated ceramic heater having a specific shape, comprising steps of:

preparing a plurality of ceramic green sheets;

laminating the plurality of ceramic green sheets to form a lamination body;

cutting the lamination body into an intermediate body having said specific shape before the lamination body is heated;

baking the intermediate body; and forming a conductive heater pattern having a terminal portion on one of the plurality of ceramic green sheets before the step of laminating the plurality of ceramic green sheets, wherein the intermediate body is formed to have a side surface on which the terminal portion is exposed by the step of cutting the lamination body.

14. The method of claim 13, further comprising, after the step of laminating the plurality of ceramic green sheets, a step of forming a through hole exposing the terminal portion of the heater pattern in the lamination body, wherein the lamination body is cut along a line that crosses the through hole to form the intermediate body having the side surface with a recess on which the terminal portion is exposed.

15. A method of manufacturing a laminated ceramic heater, comprising the steps of:

preparing first and second ceramic green sheets;

forming a heater pattern on the first ceramic green sheet, the heater pattern having a terminal portion;

laminating the first and second ceramic green sheets with the heater pattern interposed between the first and second ceramic green sheets to form a lamination body;

cutting the lamination body in such a manner that the heater pattern is cut, to form an intermediate body holding the heater pattern therein and having a side surface which is cut to expose the terminal portion of the heater pattern thereon; and baking the intermediate body.

16. The method of claim 15, wherein the lamination body is cut with a cutting device that is pushed from above.

17. The method of claim 15, wherein the step of cutting the lamination body comprises steps of:

forming a groove on a surface of the lamination body; and applying stress to the lamination body on both sides of the groove.

18. The method of claim 15, wherein in the step of forming the groove, two grooves are respectively formed on opposite surfaces of the lamination body in the same plane.

19. The method of claim 15, wherein the heater pattern has a heat portion and a lead portion.

20. The method of claim 19, wherein the heater pattern is formed to satisfy a relationship of $L \geq (A1/B1) \times W$, wherein A1 is a thickness of the heater pattern interposed between the first and second ceramic green sheets, B1 is a thickness of the terminal portion exposed on the side surface of the intermediate body, and W is a width of the lead portion of the heater pattern.

21. A method of manufacturing a ceramic heater comprising the steps of:

preparing a first ceramic green sheet;

forming a heater pattern on said first ceramic green sheet, the heater pattern including a terminal portion;

preparing a second ceramic green sheet;

laminating said first and second ceramic green sheets with said heater pattern interposed therebetween, thereby to form a laminated body;

cutting the laminated body to form an intermediate body having at least a portion of said heater pattern therein and having a side surface comprising a cut surface of said terminal portion, whereby said terminal portion of said heater pattern is exposed at said side surface of said intermediate body; and baking the intermediate body.

22. The method of claim 21, further comprising, after the step of laminating the plurality of ceramic green sheets, a step of forming a through hole in the lamination body extending through at least a portion of the terminal portion, thereby to form said cut surface of the terminal portion, and wherein during said cutting step the lamination body is cut along a line that crosses the through hole whereby the side surface of the intermediate body has a recess on which the terminal portion is exposed.

23. The method of claim 21, wherein during said cutting step said side surface of said intermediate body and said cut surface of said terminal portion are simultaneously formed.

* * * * *